(12) United States Patent
Zin

(10) Patent No.: US 6,534,324 B1
(45) Date of Patent: Mar. 18, 2003

(54) RAPID ASSAY STRIP AND METHOD OF RAPID COMPETITIVE ASSAY

(75) Inventor: Benedict L. Zin, San Diego, CA (US)

(73) Assignee: Mizuho USA, Inc., Poway, CA (US)

( * ) Notice: Subject to any disclaimer, the term of this patent is extended or adjusted under 35 U.S.C. 154(b) by 0 days.

(21) Appl. No.: 09/573,717

(22) Filed: May 12, 2000

(51) Int. Cl.[7] .............................................. G01N 33/543
(52) U.S. Cl. .......................... 436/518; 422/56; 422/57; 422/60; 422/61; 435/4; 435/7.1; 435/7.94; 435/287.1; 435/287.2; 435/287.3; 435/287.7; 435/287.9; 435/805; 435/810; 435/970; 436/514; 436/810
(58) Field of Search ............................. 422/56, 57, 60, 422/61; 435/4, 7.1, 7.94, 287.1, 287.2, 287.3, 287.7, 287.9, 805, 810, 970; 436/514, 518, 810

(56) References Cited

U.S. PATENT DOCUMENTS 5,110,550 A * 5/1992 Schlipfenbacher et al.
5,160,486 A * 11/1992 Schlipfenbacher et al.
5,728,587 A * 3/1998 Kang et al.
5,770,458 A * 6/1998 Klimov et al.
5,900,379 A * 5/1999 Noda et al.
6,001,658 A * 12/1999 Fredrickson
6,036,919 A * 3/2000 Thym et al.
6,194,221 B1 * 2/2002 Rehg et al.

FOREIGN PATENT DOCUMENTS

GB 2204398 * 11/1988

* cited by examiner

Primary Examiner—Bao-Thuy L. Nguyen
(74) Attorney, Agent, or Firm—Foley & Lardner; Bernard L. Kleinke

(57) ABSTRACT

A competitive assay strip and method of rapid competitive assay incorporating an additional step, allowing optimization or at least substantial improvement of conditions for competition between analyte conjugates and analytes or alternatively, binding of analyte, which is tailored to each particular analyte.

8 Claims, 1 Drawing Sheet

RAPID ASSAY STRIP AND METHOD OF RAPID COMPETITIVE ASSAY

BACKGROUND OF INVENTION

1. Technical Field

The present invention relates in general to a device and method for rapidly analyzing liquids for the presence of certain target chemicals. The invention more particularly relates to an apparatus and method which provides a portable, inexpensive, rapid, and yet highly accurate test for the presence of certain chemicals at predetermined threshold levels.

2. Background Art

In a variety of instances, persons wish to test liquids, and particularly biological samples, for the presence of particular chemicals. For example, water samples may be tested for the presence of particular toxins or pesticides. Similarly, such tests may be used to determine whether or not deceased or sick wildlife have been exposed to such environmental toxins. In addition, urine samples taken from individuals are tested for the presence of certain drugs, or their metabolic byproducts.

The prior-known most accurate method to test such fluids is to preserve a sample of the fluid for analysis by gas chromatography with mass spectroscopy detection ("GC/MS"). However GC/MS, although highly accurate and reliable, is extremely expensive and the large machines which perform GC/MS are not portable and require skilled labor to operate and interpret. The utilization of GC/MS therefore necessitates preservation of a biological sample taken in the field, and unwanted and undesirable delays during transportation and analysis can result in some applications.

Accordingly, portable assay strips were developed which could be used for rapid screening of biological samples in the field. Such assay strips were useful as presumptive tests for the presence of certain compounds. Samples not showing a positive result could be eliminated from further analysis, and samples showing a positive result could be readily preserved for more accurate testing by GC/MS or other methods.

In order to be useful, it was necessary that the certain threshold levels be established for the target chemical, such that an amount of the chemical below such levels did not show a positive result. As an example, the Substance Abuse and Mental Health Services Administration (SAMHSA) has developed the following guidelines for the threshold or cutoff levels of certain classes of chemicals in urine:

| Drug/Substance | Threshold (in ng/mL) |
|---|---|
| Canabinnoids metabolites | 50 |
| Cocaine metabolites | 300 |
| Opiates (morphine, codeine) | 2,000 |
| Amphetamines | 1,000 |
| Phencyclidine | 25 |

Ideally, a strip assay would always show a positive result for a drug (or drug metabolite) concentration at or above the cutoff value, and always show a negative result below the cutoff value. In reality, strip assay devices are subject to false positive and false negative results. A false positive occurs when the analyte is not present in an amount equal to or greater than the cutoff value, but the test shows a positive result. False negatives results occur when the analyte is present at a level equal to or above the cutoff, but the test shows a negative result. False positives are undesirable for a variety of reasons. For example, because all positive results are retained for additional laboratory testing (for confirmation), false positives reduce the accuracy of screening, and increase time delay and costs. False negatives are undesirable for several reasons, and in particular that they decrease the accuracy of the results.

The strip assay devices currently developed for such applications do not have sufficient accuracy to achieve the ideal, or even close to the ideal. For example, the College of American Pathologists has recommended that tests be accurate for samples within 25% of the cutoff range (i.e., that a test show no false positives at a level 25% below the cutoff, and no false negatives at a level 25% above the cutoff). However, conventional strip assays do not achieve this level of precision. Indeed, conventional assay strips are often unable to achieve accuracy within 100% of the cutoff range.

Conventional assay strips for screening for the presence of certain drug and/or drug metabolites in urine are generally constructed as competitive assay tests. These strips function by collecting an amount of urine to be analyzed. Specifically, one end of the assay strip is designed to be dipped downwardly into the urine sample and comprises a sample pad which absorbs the urine. The urine migrates along the pad. The urine is then mixed with an amount of competitor, which is generally made by conjugating the target compound with a carrier molecule (often Bovine Serum Albumin, or BSA) which has dye or other indicia means attached. Specifically, the urine flows from the sample pad into the conjugate pad, onto which an amount of competitor has been dried. Also dried onto the conjugate pad is an amount of control protein conjugated with the dye or other indicia, which provides a reference and control. The mixture is then exposed to antibodies specific to the particular analyte.

In practice, the mixture flows along a strip of nitrocellulose to which antibodies have been adhered in two rows. In the first row, antibodies specific to the particular analyte are affixed. In the second row, antibodies specific to the control protein are affixed to serve as a reference and control (showing a level of development of dye). As the mixture flows over the first row of analyte-specific antibodies, any analyte in the urine competes with the competitor for binding with the antibodies. If the level of analyte in the urine is insufficient to displace a specific amount of competitor, the dye (attached to the carrier-analyte conjugate) is seen, and the assay is read as negative. If the level of analyte in the urine is sufficient to displace the competitor to a significant degree, no dye is seen and the test is read as being a positive.

As the mixture continues to flow along the nitrocellulose strip, the second reference row is developed, and the dye is seen as the antibodies specific to the control protein bind the control protein-dye conjugate, as a reference. The assay strips also incorporate an absorbent pad at the terminus of the nitrocellulose, to absorb excess mixture.

In an alternative conventional methodology, the assay operates as above initially, except that the conjugate pad referenced is treated with antibodies specific to the analyte, conjugated with dye or other indicia. In this method, the analyte in the urine is bound by the anti-analyte antibodies in the conjugate pad, and the mixture is then allowed to flow along a nitrocellulose strip on which the first row is composed of analyte (conjugated to a carrier protein such as BSA). If the level of analyte in the urine is insufficient to saturate the anti-analyte antibodies, then the anti-analyte antibodies will bind to the immobilised analyte-BSA conjugate on the strip and the result will be read as negative. If, however, the level of analyte in the urine is sufficient to saturate the anti-analyte antibodies, these antibodies will flow over the immobilised analyte-BSA conjugate on the membrane, and the result will be read as positive. As in the first method, the mixture continues to flow along the nitrocellulose membrane, encountering the second row of antibodies, which in this method bind the antibody-dye conjugate.

Using assay strips, a urine sample can be screened within minutes after it is obtained. In practice, multiple strips (each specific for a particular analyte) are dipped into a sample, and the results obtained. In such a manner, small, relatively inexpensive, and portable assay strips can be provided to persons which enable them to screen a particular urine sample in the field for a variety of compounds. However, prior known assay strips do not achieve a level of precision which is desirable.

As discussed above, the result of an assay is determined by examining the color intensity (or other indicia) at the test line (the first row). Ideally, this line would be very intense at values below the cutoff, visible at the cutoff, and invisible for values above the cutoff. In practice, the color fades from intense to virtually invisible over some range, and this range defines the precision of the test. In conventional assay strips, the intensity of the color at the test line is virtually identical (highly intense) for analyte levels 25% below the theoretical cutoff, at the theoretical cutoff, and 25% above the theoretical cutoff. In short, conventional assay strips, while convenient, do not utilize the cutoff value desired by SAMHSA, and are incapable of achieving the precision suggested by the College of American Pathologists.

Accordingly, it would be highly desirable to have a new and improved assay strip which is small, relatively inexpensive, and portable, yet more accurate and precise than conventional assay strips.

SUMMARY OF THE INVENTION

The principal object of the present invention is to provide a new and improved assay strip and method of rapid competitive assay which is substantially more accurate and precise than prior known assay strips.

Briefly, the above and further objects of the present invention are realized by providing an assay strip and method of rapid competitive assay which incorporates an additional step, allowing optimization or at least substantial improvement of conditions for competition between analyte conjugates and analytes which is tailored to each particular analyte. As a result, the competitive strip assay can be performed while achieving far greater accuracy and precision.

BRIEF DESCRIPTION OF DRAWINGS

The above mentioned and other objects and features of this invention and the manner of attaining them will become apparent, and the invention itself will be best understood by reference to the following description of an embodiment of the invention in conjunction with the accompanying drawings, wherein.

BEST MODE FOR CARRYING OUT THE INVENTION

Figure 1:
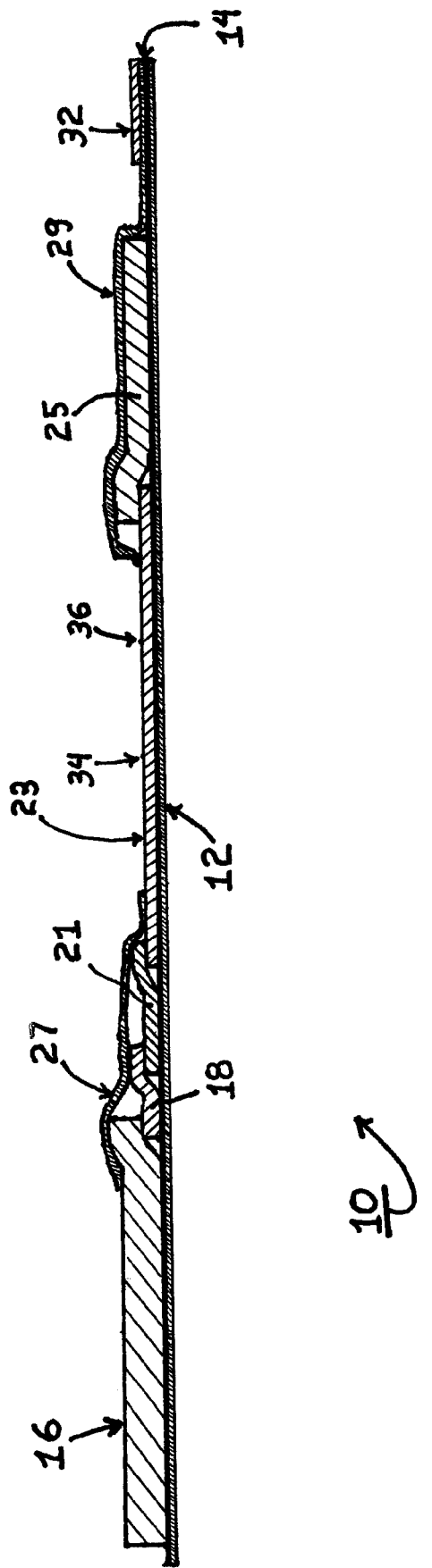
FIG. 1 a disgranmatic side elevational sectional view of an assay strip which is constructed in accordance with the present invention.

In accordance with the present invention, a rapid assay strip and method of rapid competitive assay incorporates the inclusion of a step wherein the competitive conjugate and urine mixture are introduced into a buffered solution for a period of time wherein the composition of the buffer and the period of time can be optimized for each particular analyte. In an assay strip constructed in accordance with the present invention, an additional pad is provided, as a bridge between the conjugate pad and the nitrocellulose strip. The dimensions of the bridge are optimized (in terms of length and depth) to achieve a flow at a rate optimal for a particular analyte. In addition, the bridge is treated with a particular buffer at a certain concentration which is also optimized for each analyte. In the method, a sample to be analyzed, mixed with conjugate, is reacted in a buffer for a length of time, where the composition of the buffer and the length of time are optimized for each particular analyte. As a result, the present invention allows rapid strip assay of samples while achieving a level of precision and accuracy previously unavailable.

In practice assay strips constructed in accordance with the teachings of the present invention show a highly intense color at the test line for levels of analyte 25% below the cutoff value, a visible color at the test line for levels of analyte at the cutoff value, and no color visible to the naked eye at the test line for levels of analyte 25% above the cutoff value.

Referring now to the drawings, and more particularly to FIG. 1 thereof, there is shown an assay strip 10 which comprises an elongated generally rectangular backing strip 12 covered by an adhesive layer 14 upon which are mounted various components of the assay strip. As shown and described herein, a generally rectangular sample pad 16 is mounted on the backing by the adhesive at the front end of the strip for receiving an amount of liquid to be assayed (not shown). The opposite end of the sample pad 16 overlaps the forward end of a conjugate pad 18. The conjugate pad 18 is mounted to the backing strip 12 by the adhesive layer 14 such that the forward portion of the conjugate pad is adhered to the backing strip 12, while the rearward end overlaps the forward portion of a bridge 21. The bridge 21 is affixed to the backing strip 12 by the adhesive layer 14 such that the forward end of the bridge 21 is adhered to the backing strip 12, while the rearward end of the bridge 21 overlaps the forward end of the display membrane 23.

The display membrane 23 is mounted on the backing strip 12 by the adhesive layer 14 throughout its entire length. A rearwardly disposed absorbent pad 25 is mounted on the backing strip 12 such that its forward end overlaps the display membrane 23 and extends rearwardly therefrom, adhered to the backing strip 12 by the adhesive layer 14. A coversheet 27 is adhered to the top of the sample pad 16 at a point slightly below where the sample pad 16 overlaps the conjugate pad 18, extending upwardly therefrom and adhering to the conjugate pad 18, the bridge 21 and the rearward portion of the display membrane 23.

A rearwardly disposed coversheet 29 is adhered to the rearward portion of the top of the display membrane 23, extending rearwardly therefrom and adhering to the rearward absorbent pad 25 and rearward end of the backing strip 12 and adhesive layer 14. Optionally, a drug name label 32, is adhered to the top portion of the assay strip 10 with indicia (not shown) indicating the particular analyte the assay strip is designed to detect. Any or all of the pads may be composed of suitable material such as fiberglass or other absorbent material of a variety of thicknesses and densities and may, optionally, be treated with any of a variety of surfactants.

In the preferred embodiment, the backing strip 12 comprises a vinyl material or other suitable material of a length approximately equal to 78 mm. All components are equal in width, and in the preferred embodiment, are approximately 4 mm wide. The adhesive layer 14 may be any adhesive material which is essentially inert in the conditions of the assay. The sample pad 16 is composed of an absorbent material, such as fiberglass, so that an aliquot of liquid may be placed thereon, which will wick upwardly through the pad 16 when the device is inserted vertically with its forward end disposed in the liquid under test. In the preferred embodiment, the forward end of the sample pad 16 is disposed approximately 1 mm from the forward end of the backing strip 12, extending therefrom rearwardly approximately 22 mm.

Considering now the conjugate pad 18 in greater detail, the conjugate pad 18 is composed of fiberglass, or other suitable absorbent material upon which has been deposited a competitor solution. In the preferred embodiment, the conjugate pad 18 is adhered to the adhesive layer 14 approximately 1 mm below the rear terminus of the sample pad 16, and extends rearwardly therefrom approximately 6 mm.

The competitor solution generally comprises competitor conjugate suspended in a suitable buffer. In one embodiment, the competitor conjugate is formed by conjugating a particular analyte to a suitable carrier moiety. As will be readily apparent to those skilled in the art, the carrier moiety may be Bovine Serum Albumin (BSA) or some other suitable moiety. In an alternative embodiment, the competitor solution comprises anti-analyte antibodies suspended in a suitable buffer.

In order that the results may be visualized, it is preferable to have indicia means, such as a visible dye, conjugated to the competitor conjugate. As will be readily apparent to those skilled in the art, the indicia means may be any of a variety of commercially-available colloidal gold products, or other suitable dyes. Moreover, those of ordinary skill in the art will readily comprehend that a threshold or cutoff value for any analyte can be determined and set through titration of a variety of concentrations of the competitor conjugate deposited on the conjugate pad. In this manner, a conjugate pad can be created which will provide the appropriate result for a particular cutoff value.

Considering now the bridge 21 in greater detail, the bridge is composed of fiberglass or other suitable absorbent material which has been treated with an appropriate buffer. Through titration and substitution, the buffer conditions can be optimized for a particular analyte. In accordance with the teachings of the present invention, the following buffer compositions have been developed for detecting particular analytes in urine:

In the case of phencyclidine, the preferred buffer has been determined to be approximately 50 mM Tris at pH 8.5 with 0.1% Tween 20. For cocaine metabolites, the preferred buffer has been determined to be approximately 9 mM Phosphate Buffered Saline (PBS) at pH 8.5 with 0.2% Tween 20. For amphetamines, the preferred buffer has been determined to be approximately 50 mM Tris at pH 8.5 with 1.5% Tween 20.

In accordance with the present invention, optimal buffer conditions for any analyte may be determined through titration, substitution of an appropriate surfactant. Also, the present invention allows tailoring of the length and thickness of the bridge to optimize reaction conditions and temporal effects. In accordance with the teachings of the present invention, the following dimensions have been determined to be optimal for detecting particular analytes in urine: For amphetamines, utilizing the buffer disclosed above, the preferred length of the bridge is approximately 5 mm. For cocaine and phencyclidine, using the buffers disclosed above, the preferred length of the bridge is approximately 7 mm. According to the present invention, the utilization of a bridge allows for changes of buffer composition, pH, amount and composition of surfactant, and variations in reaction time that can optimize conditions for a competitive assay of a particular analyte.

Considering now the display membrane 23 in greater detail, the display membrane 23 is composed of nitrocellulose or other suitable material to which proteins have been attached. Those skilled in the art will apprehend that the display membrane 23 may be composed of any one of a variety of absorbent materials, and that the proteins may be attached to, or deposited on, the display membrane 23.

In one embodiment, antibodies specific to the analyte are disposed on the display membrane 23 at the result line, generally indicated at 34. In the alternative embodiment, analyte conjugated to a carrier protein is disposed on the display membrane 23 at the result line 34.

Preferably, the display membrane 23 also includes a reference line, generally indicated at 36. Antibodies specific to mouse protein, are disposed at the reference line 36 to serve as a reference mark and control. As is readily apparent to those of ordinary skill in the art, in operation, dye or other appropriate indicia should always be visualized at the reference line (whether the screen yields a positive or negative result), and therefore the reference line serves a both a control (indicating generally that the reagents were still adequately active) and a reference (as to the intensity of color which should be visualized on the result line). In the preferred embodiment, the display membrane 23 is disposed approximately 31 mm from the front of the backing strip 12 (overlapped approximately 1.5 mm by the bridge 21 at the forward end), extending rearwardly therefrom approximately 25 mm (overlapped approximately 2 mm by the rearward absorbent pad at the rearward end). In the preferred embodiment, the result line 34 is located approximately 11 mm from the forward end of the display membrane 23, and the reference line 36 is located approximately 17 mm from the forward end of the display membrane 23.

In the preferred embodiment, the rearward absorbent pad 25 is comprised of fiberglass, or other suitable absorbent material, overlaps the display membrane 23 by approximately 2 mm, and extends rearwardly therefrom for approximately 15 mm. In the preferred embodiment, the front coversheet 27 and rear coversheet 29 are comprised of adhesive label material or other suitable material which protect the assay strip components from becoming dislodged during storage, transportation, and use. In the preferred embodiment, the front coversheet 27 is adhered to the top of the rear portion of the sample pad 16 at a position forward of the location of the conjugate pad 18, preferably approximately 16 mm from the forward end of the backing strip 12, and extends rearwardly therefrom, adhering to the top surfaces of the conjugate pad 18, the bridge 21, and a portion of the display membrane 23 approximately 35 mm from the front of the backing strip 12. In the preferred embodiment, the rear coversheet 29 is adhered to the top of the rear portion of the conjugate pad 18, preferably approximately 52 mm from the front of the backing strip 12, and extends rearwardly therefrom to the rear of the backing strip. As discussed, the preferred embodiment also comprises a drug name label 32 adhered to the rear portion of the assay strip 10, with indicia indicating which analyte the particular strip is designed to detect.

In operation, assay strips are prepared in accordance with the teaching of the present invention such that individual strips are prepared corresponding to a particular analyte of interest. As seen above, strips are prepared such that the conjugate pad 18 is treated with a competitive mixture corresponding to the analyte of interest. The strip also is prepared such that the bridge 21 is optimized for that particular analyte. In addition, the display membrane 23 is prepared with protein at the result line 34 corresponding to the particular analyte. The assay strip 10 may then be used for screening.

In screening, an assay strip 10 or strips corresponding to the analyte(s) of interest are dipped into the fluid to be analyzed, such that the frontal portion of the sample pad 16 is immersed in the fluid. The fluid travels up the sample pad 16 by wicking and/or capillary action until it reaches the area of overlap with the conjugate pad 18. The fluid then enters the conjugate pad 18, begins to dissolve and mix with the competitor conjugate, and continues to travel rearwards as a competition mixture. As it migrates, the competition mixture next encounters the bridge 21. The competition mixture then enters the bridge 21, dissolving the buffer salts and encountering the surfactants which were deposited on the bridge during the preparation, as described above, becoming a reaction mixture. The reaction mixture continues to travel rearwardly through the bridge 21 and into the display membrane 23. As the reaction mixture travels through the display membrane 23, the reaction mixture encounters the result line 34 where protein has been deposited in the preparation stage, as described above.

In one embodiment, the antibodies deposited on the display membrane 23 at the result line 34 will bind to competitor conjugate and/or and analyte present in the reaction mixture. In the alternative embodiment competitor conjugate (anti-analyte antibodies) which has not bound with analyte present in the urine will bind to the protein-analyte conjugate immobilised on the display membrane 23 at the result line 34.

The reaction mixture then continues to travel rearwards in the display membrane 23, next encountering the reference line 36 where, as indicated above, different antibodies, specific to mouse proteins have been deposited. Those skilled in the art will anticipate that the antibodies deposited at the reference line 36 bind mouse antibodies, which should always be present in the reaction mixture.

The reaction mixture then continues to migrate rearwardly through the display membrane 23 until it reaches the rearward absorbent pad 25, at which time it enters the rearward absorbent pad 25 and then migrates to the terminus of the rearward absorbent pad.

After sufficient time is allowed for development of the color or indicia, the assay strip 10 may be examined. When the analyte is present in the tested fluid at a level at or above the predetermined cutoff concentration, color or other indicia is seen at the reference line 36, but color or indicia is either not be visualized at the result line 34, or is visualized at a lesser intensity than the reference line 36. Alternatively, where color or indicia are visualized at the result line 34 in an intensity equal to or greater than the intensity at the reference line 36, the analyte is not present in the sampled fluid at a concentration equal to or greater than the cutoff value.

Although the disclosed embodiment of the present invention relates to test strips for screening urine for the presence of drugs and/or drug metabolites, those skilled in the art will discern that the present invention has widespread applicability to any competitive assay. More specifically, the present invention discloses a device and method which allow any strip assay to be customized for a particular analyte in a particular fluid by allowing one or more changes of buffer composition, pH, and concentration and a variety of incubation times of the reaction mixture containing the analyte and the competitor conjugate.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A system for screening fluid samples for the presence of a compound of interest, comprising:

an elongated backing strip;

a sample pad, having a forward end and a rearward end, for receiving an aliquot of the liquid to be tested, said sample pad being composed of an absorbent material;

a conjugate pad, having a forward end and a rearward end, for receiving liquid flowing from said sample pad, said conjugate pad being composed of an absorbent material and disposed so that the forward end of said conjugate pad is in fluid communication with the rearward end of said sample pad when said conjugate pad and said sample pad are wet;

said conjugate pad having deposited thereon a conjugate solution of concentration C;

a bridge for receiving liquid flowing from said conjugate pad, said bridge having a forward end and a rearward end, and being composed of an absorbent material and disposed so that the forward end of said bridge is in fluid communication with the rearward end of said conjugate pad when said bridge and said conjugate pad are wet;

said bridge having deposited thereon, a buffer and having a length L and thickness T;

a display membrane having deposited thereon an immobilized protein, said display membrane having a forward end and a rearward end, and being composed of an absorbent material and being disposed such that the forward end of said membrane is in fluid communication with the rearward end of said bridge when said membrane and said bridge are wet; and said concentration C, said buffer, said length L, and said thickness T being adapted to be independently adjustable parameters to optimize the system for detecting a particular compound of interest at a particular concentration.

2. The system according to claim 1, further comprising:

a rearward absorbent pad, adapted for receiving liquid, said rearward absorbent pad being composed of absorbent material and being disposed so that a forward end of said rearward absorbent pad is in fluid communication with said display membrane when said rearward absorbent pad and said display membrane are wet.

3. The system according to either one of claims 1 or 2 wherein said conjugate solution includes a conjugate including: the compound of interest, a carrier protein, and indicia means; and said immobilized protein includes antibodies specific to the compound of interest.

4. The system according to either one of claims 1 or 2 wherein:

said conjugate solution includes a conjugate including an antibody specific to the compound of interest and indicia means; and said immobilized protein includes a conjugate including the compound of interest and means for immobilizing said compound of interest on said display membrane.

5. The system according to claim 4 wherein said means for immobilizing comprises conjugating the compound of interest with a protein carrier and adhering said protein carrier-compound of interest conjugate on said display membrane.

6. The system according to claim 4 where:

said buffer is approximately 50 mM tris(hydroxymethyl) aminomethane at a pH of approximately 8.5; and said buffer includes approximately 0.1% polyoxyethylenesorbitan monolaurate.

7. The system according to claim 4 wherein:

said buffer is approximately 50 mM tris(hydroxymethyl) aminomethane at a pH of approximately 8.5; and said buffer includes approximately 1.5% polyoxyethylenesorbitan monolaurate.

8. The system according to claim 4 wherein:

said buffer is approximately 50 mM Phosphate Buffered Saline at a pH of approximately 8.5; and said buffer includes approximately 0.2% polyoxyethylenesorbitan monolaurate.

* * * * *